(12) United States Patent
Baiu (10) Patent No.: US 10,034,651 B2
(45) Date of Patent: *Jul. 31, 2018

(54) BRAIN TISSUE EQUIVALENT MATERIAL AND PHANTOM DEVICE COMPRISING THE SAME

(71) Applicant: Gammex, Inc., Middleton, WI (US)

(72) Inventor: Cristel Baiu, Madison, WI (US)

(73) Assignee: Gammex, Inc., Middleton, WI (US)

( * ) Notice: Subject to any disclaimer, the term of this patent is extended or adjusted under 35 U.S.C. 154(b) by 202 days.

This patent is subject to a terminal disclaimer.

(21) Appl. No.: 14/802,000

(22) Filed: Jul. 17, 2015

(65) Prior Publication Data

US 2016/0015356 A1 Jan. 21, 2016

Related U.S. Application Data

(60) Provisional application No. 62/026,392, filed on Jul. 18, 2014.

(51) Int. Cl.
*A61K 49/04* (2006.01)
*A61B 6/00* (2006.01)
*G09B 23/28* (2006.01)
*A61B 6/03* (2006.01)

(52) U.S. Cl.
CPC ............ *A61B 6/583* (2013.01); *G09B 23/286* (2013.01); *A61B 6/032* (2013.01); *A61B 6/501* (2013.01); *A61B 6/54* (2013.01)

(58) Field of Classification Search
None
See application file for complete search history.

(56) References Cited

U.S. PATENT DOCUMENTS

| | | |
|---|---|---|
| 5,335,260 A | 8/1994 | Arnold |
| 5,625,137 A | 4/1997 | Madsen et al. |
| 5,902,748 A | 5/1999 | Madsen et al. |
| 6,190,915 B1 | 2/2001 | Madsen et al. |
| 6,238,343 B1 | 5/2001 | Madsen et al. |
| 6,352,860 B1 | 3/2002 | Madsen et al. |
| 6,974,254 B2 | 12/2005 | Paliwal et al. |
| 7,252,434 B2 | 8/2007 | Jaradat |
| 8,480,407 B2 | 7/2013 | Campbell et al. |
| 8,517,608 B1 | 8/2013 | Arnold |
| 8,588,365 B2 | 11/2013 | Lang et al. |

OTHER PUBLICATIONS

Hill (Phys. Med. Biol. 2005, 50, N331-N344).*
Yohannes et al. (Phys. Med. Biol. 2012, 57, 1173-1190).*
Chong et al, "Separation of bone from iodine- and gadolinium-based contrast agents using dual energy CT", Physics of Medical Imaging, vol. 6913, 2008.
Civ, "Tissue Substitues in Radiation Dosimetry and Measurement (Report 44)", Commission Meeting 2014. http://icru.org/home/reports/tissue-substitutes-in-radiation-dosimetry-and-measurement-report-44.
Hubbell et al., "Tables of X-Ray Mass Attenuation Coefficients and Mass Energy-Absorption Coefficients from 1 keV to 20 MeV for Elements Z=1 to 92 and 48 Additional Substances of Dosimetric Interest", Radiation Physics Division, Table 4, Brain, Grey/White Matter, U.S. Secretary of Commerce on behalf of the United States of America, 1996.
Liu et al., "Evaluation of two water-equivalent phantom materials for output calibration of photon and electron beams" Med. Dosim, vol. 28, No. 4, Abstract, 2003.
Ramaseshan et al., "Dosimetric evaluation of Plastic Water Diagnostic Therapy", Journal of Applied Clinical Medical Physics, vol. 9; No. 2, 2008.
Thomadsen et al., "Evaluation of water-equivalent plastics as phantom material for electron-beam dosimetry", Med. Phys., vol. 22, No. 3, 1995.
White et al, "Epoxy resin based tissue substitutes", British Journal of Radiology, vol. 50, pp. 814-821, 1977.
Yohannes et al., "A formulation of tissue- and water-equivalent materials using the stoichiometric analysis method for CT-number calibration in radiotherapy treatment planning", Physics in Medicine and Biology, 57: pp. 1173-1190, 2012.
Gammex Solid Water and TEM Guide by Gammex, Inc., Feb. 2012.
Certified Therapy Grade Solid Water by Gammex, Inc., Jun. 2008.
Convenient Packages of Solid Water by Gammex, Inc., Sep. 2010.
Certified Therapy Grade Solid Water, Gammex 457-CTG, by Gammex, Inc., http://www.gammex.com/n-portfolio/productpage.asp?id=287&category=Radiation Oncology&name=Certified Therapy, website visited 2014.
Tissue Equivalent Materials by Gammex, Inc., Jun. 2008.
Tissue Characterization Phantom, Model 467 User's Guide by Gammex, Inc., 2004.

* cited by examiner

*Primary Examiner* — Michael G Hartley
*Assistant Examiner* — Melissa J Perreira
(74) *Attorney, Agent, or Firm* — Andrus Intellectual Property Law, LLP (57) ABSTRACT

Compositions, including composition for use in radiographic calibration and quality assurance include glass micro bubbles, epoxy, $CaCO_3$, MgO, and Polyethylene. Embodiments of the composition may be used in calibration devices or phantoms. Calibration devices or phantoms constructed of embodiments of the composition may be used in methods of calibrating a radiographic device for imaging of brain tissue.

18 Claims, 5 Drawing Sheets

BRAIN TISSUE EQUIVALENT MATERIAL AND PHANTOM DEVICE COMPRISING THE SAME

CROSS-REFERENCE TO RELATED APPLICATION

The present application claims priority of U.S. Provisional Patent Application No. 62/026,392, filed on Jul. 18, 2014, the content of which is hereby incorporated herein by reference in its entirety.

BACKGROUND OF THE INVENTION

The present disclosure is related to the field of radiographic imaging, radiotherapy and analysis thereof. More specifically, the present disclosure is related to phantoms/material, and methods of using these phantoms for radiological purposes.

X-rays and other radiological techniques are important diagnostic and therapeutic tools. However, the measurement of absorbed doses within and around irradiated body tissues necessitates calibration of these radiographic devices with phantoms constructed of carefully selected materials. The use of such phantoms permits determination of absorbed doses when information on the energy and nature of the charged particles at the point of interest is incomplete or fragmentary.

The International Commission on the Radiation Unit and Measurements (ICRU) in its report entitled "Tissue Substitutes in Radiation Dosimetry and Measurement" provides approximate elemental, radiographic, and other physical properties for average body tissues, including brain tissue. The report provides physical quantities for consideration in the selection of tissue substitutes for dosimetric studies and other measurements involving photons, electrons, neutrons, and heavy charged particles. The report further provides the elemental compositions, mass densities, and electron densities of average body tissues. The report also includes recommended elemental compositions in physical characteristics for tissue substitutes. For example, the ICRU Report 44 suggests a brain composition of 10.7% hydrogen, 14.5% carbon, 2.2% nitrogen, 71.2% oxygen, 0.3% chlorine, 0.2% sodium, 0.2% sulfur, 0.4% phosphorus, and 0.3% potassium. The report also notes that the average brain tissue has a physical density of 1.040 $g/cm^3$.

The inventor has recognized that previous attempts at modeling brain tissue for phantoms for use in calibration or dosimetry procedures have typically been accurate at specific imaging energies. However, with the increase in prevalence of low dose radiographic imaging, particularly low-dose CT imaging, and multiple energy CT imaging, a brain tissue phantom that accurately exhibits the radiographic properties of brain tissue over a wide range of X-ray energies is required.

A further challenge to the development of radiographic phantoms of brain tissue is to minimize the inherent compositional differences between actual brain tissue and the brain-equivalent material, yet provide a material that is solid and usable as a phantom at standard temperature and pressure. A typical brain phantom material is constructed of an epoxy, acrylic, or polyethylene base, which is modified by other elements to achieve a desired elemental composition, physical density, effective atomic number, electron density, and radio density such that the attenuating and scattering characteristics closely resemble that of brain tissue.

SUMMARY OF THE INVENTION

The present disclosure is related to the field of radiographic imaging, radiotherapy, radiodiagnostics, calibration of devices for use in these applications, treatment planning as well as other applications. More specifically, the present disclosure is related to brain tissue equivalent materials and phantoms constructed thereof for calibration and/or quality assurance purposes in radiology. In particular, the compositions are brain tissue equivalent materials.

An exemplary embodiment of a brain tissue equivalent phantom comprises hydrogen at a concentration of 5-10% or 8-9% (w/w) and carbon at a concentration of 60-80% or 67-68% (w/w). The calibration device further includes nitrogen at a concentration of 0.5-4% or 1-2% (w/w) and oxygen at a concentration of 12-25% or 20-21% (w/w). The calibration device may further include up to 1% (w/w) of each of chlorine, calcium, and silicon.

In another exemplary embodiment, the brain tissue equivalent phantom composition includes 1.6-3.6% glass micro bubbles (w/w), 50-63% Araldite (w/w), 18-24% Jeffamine (w/w), 3-5% $CaCO_3$ (w/w), 1-3% MgO (w/w); and 9-13% Polyethylene (w/w). The composition may further include 3-7% acrylic microspheres (w/w) and/or 0-1% pigment. The composition may have an elemental composition including hydrogen at a concentration of 8-9% (w/w), carbon at a concentration of 67-68% (w/w), nitrogen at a concentration of 1-2% (w/w), oxygen at a concentration of 20-21% (w/w), chlorine at a concentration of less than 1% (w/w), calcium at a concentration of less than 1% (w/w), and silicon at a concentration of less than 1% (w/w).

In yet another exemplary embodiment, the brain tissue equivalent phantom composition includes 1-4% glass micro bubbles (w/w), 60-80% epoxy, 3-5% $CaCO_3$ (w/w), 1-3% MgO (w/w); and 9-13% Polyethylene (w/w). The epoxy components may be present in a 10:4 to 1:1 ratio of resin to polyamine or any hydride. The composition may further include 3-7% acrylic microspheres (w/w) and/or 0-1% pigment. The composition may have an elemental composition including hydrogen at a concentration of 8-9% (w/w), carbon at a concentration of 67-68% (w/w), nitrogen at a concentration of 1-2% (w/w), oxygen at a concentration of 20-21% (w/w), chlorine at a concentration of less than 1% (w/w), calcium at a concentration of less than 1% (w/w), and silicon at a concentration of less than 1% (w/w).

In a further exemplary embodiment of a brain tissue equivalent phantom, the phantom consists of hydrogen at a concentration of 8.56% (w/w), carbon at a concentration of 6-7.46% (w/w), nitrogen at a concentration of 1.82% (w/w), oxygen at a concentration of 20.52% (w/w), chlorine at a concentration of 0.11% (w/w), calcium at a concentration of 0.75% (w/w), silicon at a concentration of 0.64% (w/w), boron at a concentration of 0.02% (w/w), and sodium at a concentration of 0.10% (w/w).

In a still further exemplary embodiment of a calibration device, the calibration device comprises 1.6-3.6% glass micro bubbles (w/w), 50-63% Araldite (w/w), 18-24% Jeffamine (w/w), 3-5% $CaCO_3$ (w/w), 1-3% MgO (w/w), 9-13% Polyethylene (w/w), 3-7% Acrylic Micro Spheres (w/w), 0-1% Pigment (w/w). In one embodiment, the calibration device comprises about 50-80% of the combination of Araldite and Jeffamine and 4-6% Acrylic microspheres.

A still further exemplary embodiment of a calibration device includes a phantom base which includes a plurality of slots. Each slot in the phantom base is configured to receive a tissue phantom. A brain tissue phantom is configured to be received into a slot of the plurality of slots. The brain tissue phantom includes hydrogen at a concentration of 5-10% or 8-9% (w/w) and carbon at a concentration of 60-80% or 67-68% (w/w). The brain tissue phantom further includes oxygen at a concentration of 12-25% or 20-21% (w/w) and nitrogen at a concentration of 0.5-4% or 1-2% (w/w). The brain tissue phantom also includes up to 1% (w/w) each of at least chlorine, calcium, and silicon, boron, and sodium.

An exemplary embodiment of a calibration device includes a body formed of at least a first portion of a first material having a first radiographic property and a second portion of a second material having a second radiographic property. A dial is rotatably secured within the body. The dial includes at least one slot therein. At least one insert is located in the at least one slot. The dial is rotatable to physically position the at least one insert relative to the first portion.

An exemplary embodiment of a method of calibrating a radiographic device for imaging of brain tissue includes providing a phantom with a brain equivalent material. The brain equivalent material includes hydrogen at a concentration of 5-10% or 8-9% (w/w), carbon at a concentration of 60-80% or 67-68% (w/w), nitrogen at a concentration of 0.5-4% or 1-2% (w/w), oxygen at a concentration of 12-25% or 20-21% (w/w), and less than 1% (w/w) each of chlorine, calcium, and silicon, boron, and sodium. The phantom is aligned with the radiographic device. An attenuation of X-rays by the brain equivalent material is measured. A device specific correction factor is calculated for the radiographic device from the measured attenuation of the X-rays and a known electron density for the brain equivalent material.

DETAILED DISCLOSURE

A phantom for use in calibration and dosimetry in radiographic applications, including computer tomography (CT) imaging mimics the radiographic properties of brain tissue. The disclosed embodiments of the brain tissue mimicking phantom advantageously exhibit the radiographic properties of brain tissue over a wide range of radiographic imaging energies and particularly are effective at modeling the radiographic properties of brain tissue at energies less than 100 keV electron volts, and in further embodiments, less than 80 keV. Often, medical radiology uses X-rays between 5-150 keV and CT are typically performed at or above 100 keV. With the advent of low dose CT imaging and dual or multiple energy CT imaging, phantoms representative of radiographic properties of brain tissue over a wider range of X-ray energies are desired.

In one embodiment the composition comprises 1.6-3.6% glass micro bubbles (w/w), 50-63% Araldite (w/w), 18-24% Jeffamine (w/w), 3-5% $CaCO_3$ (w/w), 1-3% MgO (w/w), and 9-13% Polyethylene (w/w). The compositions may also include 3-7% Acrylic Micro Spheres (w/w), and/or 0-1% Pigment (w/w). The composition may have an elemental composition including hydrogen at a concentration of 8-9% (w/w), carbon at a concentration of 67-68% (w/w), nitrogen at a concentration of 1-2% (w/w), oxygen at a concentration of 20-21% (w/w), chlorine at a concentration of less than 1% (w/w), calcium at a concentration of less than 1% (w/w), and silicon at a concentration of less than 1% (w/w).

In one embodiment, the composition comprises about 50-80% of the combination of Araldite and Jeffamine. The Araldite to Jeffamine ratio may be 10 to 4, 12.5 to 10 or 1 to 1. Thus within these ranges the Araldite and Jeffamine comprise the majority of the composition. The Jeffamine may have a molecular weight of about 440. The composition may further comprise 4-6% Acrylic microspheres and may further comprise 1-4% glass micro bubbles, suitably 1.6-3.6% glass micro bubbles. The compositions may further include about 3% calcium (provided as calcium carbonate) and about 2% magnesium (provided as magnesium oxide). The composition is made by mixing the dry constituents together prior to formation of the epoxy.

In an alternative embodiment, the brain tissue equivalent phantom composition includes 1-4% glass micro bubbles (w/w), 60-80% epoxy, 3-5% $CaCO_3$ (w/w), 1-3% MgO (w/w); and 9-13% Polyethylene (w/w). The epoxy components may be present in a 10:4 to 1:1 ratio of resin to polyamine or any hydride. The epoxy resin may be selected from Araldite, trimethyihexamethylenediamine, Epoxide No. 7, Epikote and combinations thereof. Those of skill in the art will appreciate that other resins could be used in place of those provided herein. The hardener may be selected from Jeffamine, Synolide, aminohexanes, polyoxypropylenetriamines or combinations thereof. Those of skill in the art will appreciate that other hardeners could be used in place of those provided herein. The composition may further include 3-7% acrylic microspheres (w/w) and/or 0-1% pigment. The composition may have an elemental composition including hydrogen at a concentration of 8-9% (w/w), carbon at a concentration of 67-68% (w/w), nitrogen at a concentration of 1-2% (w/w), oxygen at a concentration of 20-21% (w/w), chlorine at a concentration of less than 1% (w/w), calcium at a concentration of less than 1% (w/w), and silicon at a concentration of less than 1% (w/w).

The compositions may also include optionally boron, sodium or a combination thereof. The boron or sodium may be present at a concentration of less than 1% (w/w) of the composition. An exemplary embodiment of the brain tissue phantom as disclosed herein includes an elemental composition of 8.56% hydrogen, 67.46% carbon, 1.82-1.85% nitrogen, 20.52% oxygen, 0.11% chlorine, 0.75% calcium, 0.64% silicon, 0.2-0.02% boron, and 0.1% sodium. Embodiments of the new brain tissue phantom have been measured to have a physical density of between 1.250-1.070 $g/cm^3$. Specific embodiments within that range my include 1.062 $g/cm^3$ or 1.050 $g/cm^3$. In a further embodiment, physical density is between 1.045 $g/cm^3$ and 1.055 $g/cm^3$. When constructed, embodiments may have a manufacturing tolerance of +/−0.005 $g/cm^3$.

The ingredients listed above assume a nominal density of the glass micro bubbles of 0.22 g/cc and results in an electron density and effective atomic number of the material within better than 0.5% from distilled water. Variation of the physical density of glass micro bubbles (typical +/−15%) requires adequate changes in the percentages of the other ingredients to maintain the physical density, electron density, effective atomic number and calculated CT number within the target. The Araldite/Jeffamine Epoxy system can be changed within a range of 100/30 proportion up to 100/100 to achieve other desired mechanical properties of the material. Specific examples include 100/40 and 100/43 ratios. The Araldite/Jeffamine epoxy system should be between 60 and 90% of the final composition. This will require the re-adjustment of the concentrations of the other ingredients.

In an embodiment, the glass microspheres are S22 Glass Bubbles available from 3M. The Glass Bubbles have an 80% size distribution between 20 microns and 65 microns and in general resemble the chemical properties of soda-lime-borosilicate glass.

ARALDITE is a structural adhesive available from Huntsman Advanced Materials. Araldite is an epoxy adhesive with high temperature and chemical resistances, low shrinking, and high resistance to water and a variety of other chemicals. Araldite GY 6010 has chemical formula $C_{21}H_{24}O_4(C_{18}H_{20}O_3)n$ and a molecular weight of 364-384. Araldyte GY 6010 has the color and consistency of honey and will also crystallize at temperatures below 18 Celsius. Warming up this material at temperatures above 60 Celcius eliminates the crystals and lowers the viscosity making it easier to degass.

Exemplarily, earth pigments or other naturally occurring pigments that either don't impact radiological characteristics or minimally impact radiological characteristics within the tolerance herein. Suitable pigments have a high tinting strength in or to be effective in a very small quantities, and have an elemental composition that contains elements with a Z number not higher than 20. Exemplarily, pigments may include earth pigments or organic dyes which include, but are not limited to polymeric, glycol, or water based pigments.

The ingredients are all weighed and placed on a mixing bowl. The mixing process takes place in a vacuumed chamber to eliminate air bubbles for about 40 minutes. The mix is then transferred in molds to create slabs or other desired forms, exemplarily as disclosed herein. Alternatively the powders can be pre-mixed with one pan of the epoxy system (e.g. Araldite) and stored until mixed with the second part of the epoxy system. Cooling down the Jeffamine at temperature around 10 Celsius before is added to the mix assures a higher viscosity and therefore a more uniform distribution of the solid ingredients (heavier ingredients will not sink and low density ingredients will not float).

In yet a further embodiment, the composition comprises hydrogen at a concentration of 5-10% or 8-9% (w/w) and carbon at a concentration of 60-80% or 67-68% (w/w). The JEFFAMINE is a polyetheramine which contains primary amino group attached to the end of a polyether backbone. The polyether backbone is normally based on propylene oxide, ethylene oxide or a mixture of propylene oxide and ethylene oxide. In an exemplary embodiment, the Jeffamine is a propylene oxide triamine prepared by the reaction of propylene oxide with triol initiator, followed by animation of the trammel hydroxyl groups and may be exemplified by the following structure:

Exemplarily, this compound has molecular weight of 440.

The polyethylene used in the compositions described herein was Microthene FN510-00 a microfine polyolefin powder with a density of 0.923 obtained from Equistar Chemicals, Houston, Tex. Other low density polyethylene powders may be substituted for the polyethylene used herein. The magnesium oxide used herein was a high purity technical grade obtained from Premier Chemicals, Middleburg Heights, Ohio. The calcium carbonate used herein was a 5 micron grain size obtained from Chidley & Petro Co., Arlington Heights, Ill. Those of skill in the art will appreciate that these materials may be substituted with others of similar grade from other suppliers.

Some embodiments may include pigments, in an amount 0-1% (w/w).

composition further includes nitrogen at a concentration of 0.5-4% or 1-2% (w/w) and oxygen at a concentration of 12-25% or 20-21% (w/w). The composition may further include up to 1% (w/w) of each of chlorine, calcium, boron and silicon. The compositions provided herein may include from 0.01 to 1% (w/w) or 0.05 to 0.5% (w/w) of each of chlorine, calcium, boron and silicon.

In testing, the disclosed brain tissue phantom provides a highly accurate representation of radiographic attenuation as represented by a CT number or Hounsfield Unit (HU) in comparison to average measures of brain tissue attenuation across a large range of X-ray energies. In embodiments, the disclosed brain tissue phantom follows the spectral curve of typical human brain tissue (50:50 gray/white matter ratio) to within ±5 HU at least across the spectral range of 10-140 keV. Embodiments of the disclosed brain tissue phantom material have further been verified across the spectral range of 40 keV-140 keV to average brain CT scan results. In still further embodiments, the disclosed brain tissue follows the same spectral curve to within ±1 HU at least across the range of 40-140 keV. Based upon testing the disclosed brain phantom material is believed to accurately represent radiographic attenuation at energies above and below this range as well.

The inventors have further discovered that the brain tissue phantom as disclosed herein is further equivalent (used herein as being within ±1%) to average brain tissue as disclosed by ICRU in physical and electron density. The compositions provided herein mimic the radiographic attenuation of brain tissue for X-ray energies between 40 keV and 140 keV. In particular the brain tissue phantom compositions provided herein are more similar to average brain tissue at energies below 120 keV, below 100 keV or below 80 keV as compared to prior brain tissue phantoms. The brain tissue phantom compositions provided herein vary from actual brain tissue by less than 25%, 22%, 20%, 18%, 15%, 12%, 10%, 8%, 7%, 6%, 5%, 4%, 3%, 2% or 1% at a particular energy and particularly at energies below 100 keV.

Figure 1:
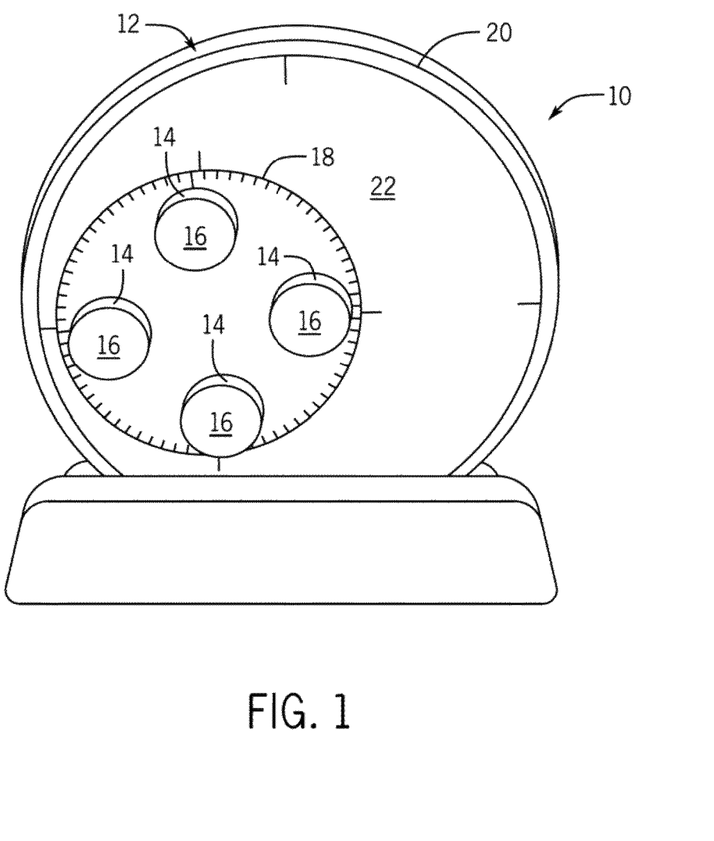
FIG. 1 depicts an exemplary embodiment of a calibration device.

FIG. 1 depicts an exemplary embodiment of a calibration device for radiographic and radio therapeutic applications. In an embodiment, the calibration device 10 includes a device body 12 within which a plurality of slots 14 as described in further detail herein extend. In an exemplary embodiment, the body 12 may be constructed of a material of a consistent and referenced material. Exemplarily, the body 12 may be constructed of a water equivalent material as the Hounsfield unit (HU) scale is defined such that 0 Hounsfield unit is equivalent to the radio density of distilled water at standard pressure and temperature. In a non-limiting embodiment, the material of the body 12 may be the SOLID WATER® water equivalent material available from Gammex, Inc. In a still further exemplary embodiment, as disclosed herein, the body 12 may be constructed, at least partially of the new brain material as disclosed herein. A plurality of tissue equivalent inserts 16 extend into the respective slots 14 in the body 12. In embodiments as will described in further detail herein, at least one of the tissue equivalent inserts 16 is a brain tissue phantom constructed of the materials and/or in the manner as disclosed in further detail herein. The remaining tissue equivalent insert 16 may also be brain tissue phantoms, or may exemplarily be tissue equivalent inserts constructed to model other tissues or structures within the body.

In an embodiment, the slots 14 are cylindrical holes and the insert 16 are cylindrical rods. Although, it will be recognized that other geometries of the slots and inserts may be recognized by a person of ordinary skill in the art.

Figure 2:
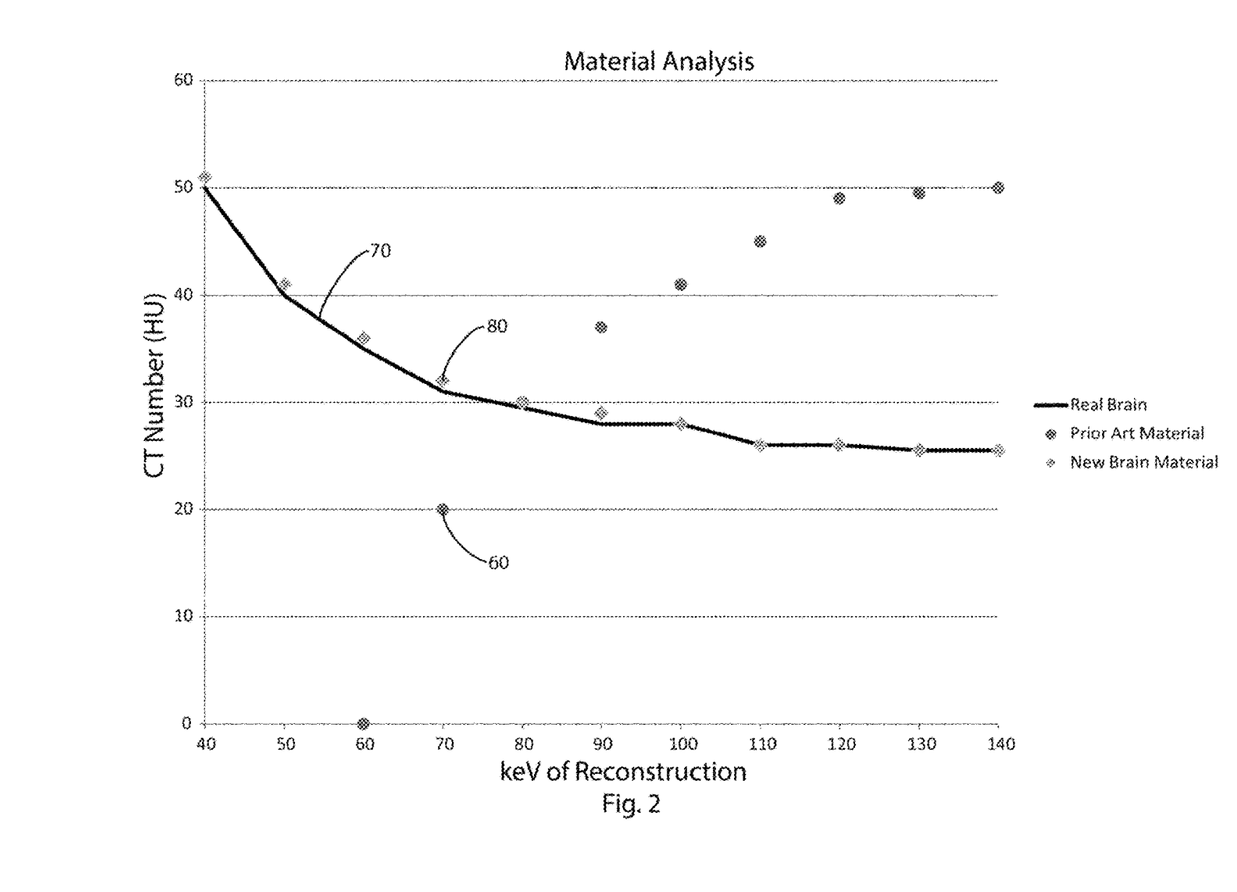
FIG. 2 depicts a graph of measured CT number versus X-ray strength for various materials.

In an additional embodiment, the calibration device 10 further includes a dial 18 which rotates within the body 12. The dial 18 includes the one or more slots 14 which are configured to receive inserts 16, which may be selected from a plurality of inserts as described in further detail herein. While the dial 18 is depicted in FIG. 2 as including four slots 14 and inserts 16, it is to be understood that this is merely exemplary and other number of one or more slots and inserts may be used in embodiments. In still further embodiments, the dial 18 may be constructed with integrally formed inserts. In an embodiment, the dial 18 may be removable from the body 12.

The body 12 may further include a first portion 20 and a second portion 22. The first portion 20 and the second portion 22 are constructed of materials having different radiographic properties, exemplarily two different tissue-equivalent materials. In non-limiting examples, any of the tissue equivalent materials available from Gammex, Inc., including, but not limited to: Cortical Bone (Gammex 450), Muscle (Gammex 452), Adipose (Gammex 453), Breast (Gammex 454), lung (Gammex 455), inner Bone (Gammex 456), liver (Gammex 482), and brain (Gammex 482) or the brain tissue materials as disclosed herein, may be used in the calibration device. In an example, the first portion 20 is dimensioned (e.g. thickness) and constructed of a material to mimic a human skull. In an example, the second portion 22 is constructed of a brain tissue equivalent material described in the present application. In additional embodiments, the body 12 may include additional portions based on the first portion 20 and the second portion 22. The additional portions may further be constructed of other tissue-equivalent materials, or a water-equivalent material.

In additional embodiments, the inserts 16 are each constructed of a tissue or water equivalent material, which may include a brain tissue equivalent material as described in the present application. In still further embodiments, an insert 16 is constructed of at least two materials and includes an auxiliary phantom embedded within the insert. In an exemplary embodiment as described in further detail herein, the auxiliary phantom is constructed of a blood-equivalent material and is shaped to mimic a vessel, an aneurysm, or a hematoma. In still further embodiments, the insert 16 is primarily constructed of the brain tissue equivalent material as described in the present application and the auxiliary phantom is embedded in the insert 16. In a still further exemplary embodiment, the auxiliary phantom is a tumor-equivalent auxiliary phantom.

In operation, at least one insert 16 including an auxiliary phantom is inserted into one of the slots 14 of the dial 18. The dial 18 is then rotated about an axis of rotation, such as to change a relative position of each of the at least one inserts 16 within the calibration device 10. In an exemplary embodiment, the axis of rotation of the dial 18 is different from a central axis of the calibration device, such that the at least one insert is moveable to a plurality of distances relative to the exterior first portion 20 of the body 12 or to another structure or additional portion located within the body 12.

In an exemplary embodiment, the first portion 20 mimics a patient's skull and at least one insert 16 includes an auxiliary phantom (e.g. an aneurysm mimicking phantom). The dial 18 is rotatable to position the auxiliary phantom (an aneurysm) relative to the first portion (skull) to replicate an orientation of interest. The orientation of interest may exemplarily mimic an anatomical location of such structures (skull, aneurysm) of a patient to be imaged. In other exemplary embodiments, the auxiliary phantom is a tumor phantom, or a plurality of inserts, each with different auxiliary phantoms are used.

In still further exemplary embodiments as described in further detail herein, embodiments of the calibration device 10 may be used in methods of calibrating a CT imaging system for both qualitative and quantitative imaging procedures. Qualitative calibration and/or quality assurance may evaluate the system's ability to accurately represent the radiographic attenuation of the patient's brain tissue in Hounsfeld Units. Further qualitative calibration and/or quality assurance can improve the identification of different tissues and structures in a CT scan. In still other embodiments, use of auxiliary phantoms may further improve the system's ability to e.g. identify an aneurysm auxiliary phantom in close proximity to the skull or to another anatomical structure represented by tissue mimicking material and/or auxiliary phantom. Qualitative calibration and/or quality assurance may improve calculations a volume of the (e.g. aneurysm) of the auxiliary phantom and this calibration compared to a known volume of the auxiliary phantom.

FIG. 2 exemplarily depicts an exemplary graph 50 representing the measured Hounsfield Units of various compositions measured at different X-ray energies across a range between 40 keV and 140 keV. Graph 70 represents a CT measurement of real brain tissue. Graph 60 is the measurement of a prior art brain tissue phantom. The measured prior art brain tissue phantom is inversely related to the graph of the measured brain tissue 70, exhibiting correspondence with the attenuation of brain tissue at only a single intersection point about 80 keV and generalized correspondence (<Δ25 HU) when the X-ray energy was above 80 keV. This inverse relationship between the CT numbers of the prior art brain phantom and the real average brain tissue results in a non-realistic contrast between the brain phantom and other tissues (e.g. blood vessels, aneurysm, or hematomas) at energies e.g. below 80 keV. Rather, across a wide range of energies and particularly at energies below 80 keV, the prior art brain phantom more closely resembled adipose tissue than brain tissue. Graph 80 represents the measured CT number (HU) of the presently disclosed brain tissue phantom. The graph 80 exhibits an accurate correspondence to the measured brain tissue over the entire range of X-ray energies as found in typical CT and Dual Energy CT scanning applications. It has been observed that embodiments of the presently disclosed brain phantom mimic the CT number of average real brain tissue within ±5 HU down to 10 keV. As exemplarily shown in FIG. 2, the presently disclosed brain phantom material has been validated by comparison to a normal brain tissue spectral curve across the entire energy range of 40 keV to 140 keV.

This result is further surprising to the inventor as the prior art brain tissue phantom more closely represented the elemental composition and physical density of actual brain tissue as defined by the ICRU Report 44. Rather, the inventors discovered that electron density and CT number of the brain tissue could be more closely mimicked at the expense of similarly to brain tissue in physical density and/or composition. Furthermore, the newly disclosed brain phantom material adds amounts of calcium, silicon, and boron that are not found in average real brain tissue according ICRU Report 44, or for example, as disclosed by D. R. White, "Epoxy resin based tissue substitutes" *British Journal of Radiology*, 50, 81-821, 1977, or C. Constantinou, "Tissue substitutes for particle radiations and their use in radiation dosimetry and radiotherapy" Diss. 1978.

Additionally, the newly disclosed brain phantom material adds Acrylic micro spheres and glass micro bubbles which decrease CT number homogeneity of the resulting material on a micro level. While Acrylic microspheres had been used in some applications, the concentration of Acrylic microspheres in the presently disclosed brain material is greatly reduced, resulting in improved attenuation at low energies. Typically, a phantom material is desired to be homogeneous, however, the inventors have found this combination of additives to more accurately mimic actual results of brain imaging and across a wider range of imaging energies. Glass micro bubbles provide a further quality of reducing total physical density of embodiments of the brain phantom material disclosed herein. The incorporation of the acrylic microspheres and glass micro bubbles affect the overall concentrations of other constituents in the brain phantom material, and introduce an intra-material variation in localized CT number. However, it has been discovered by the inventors that this intra-material variation more accurately reflects natural variation in brain tissue. Improved CT calibration and quality assurance can be achieved due to an improved correspondence with the real brain tissue.

Figure 3:
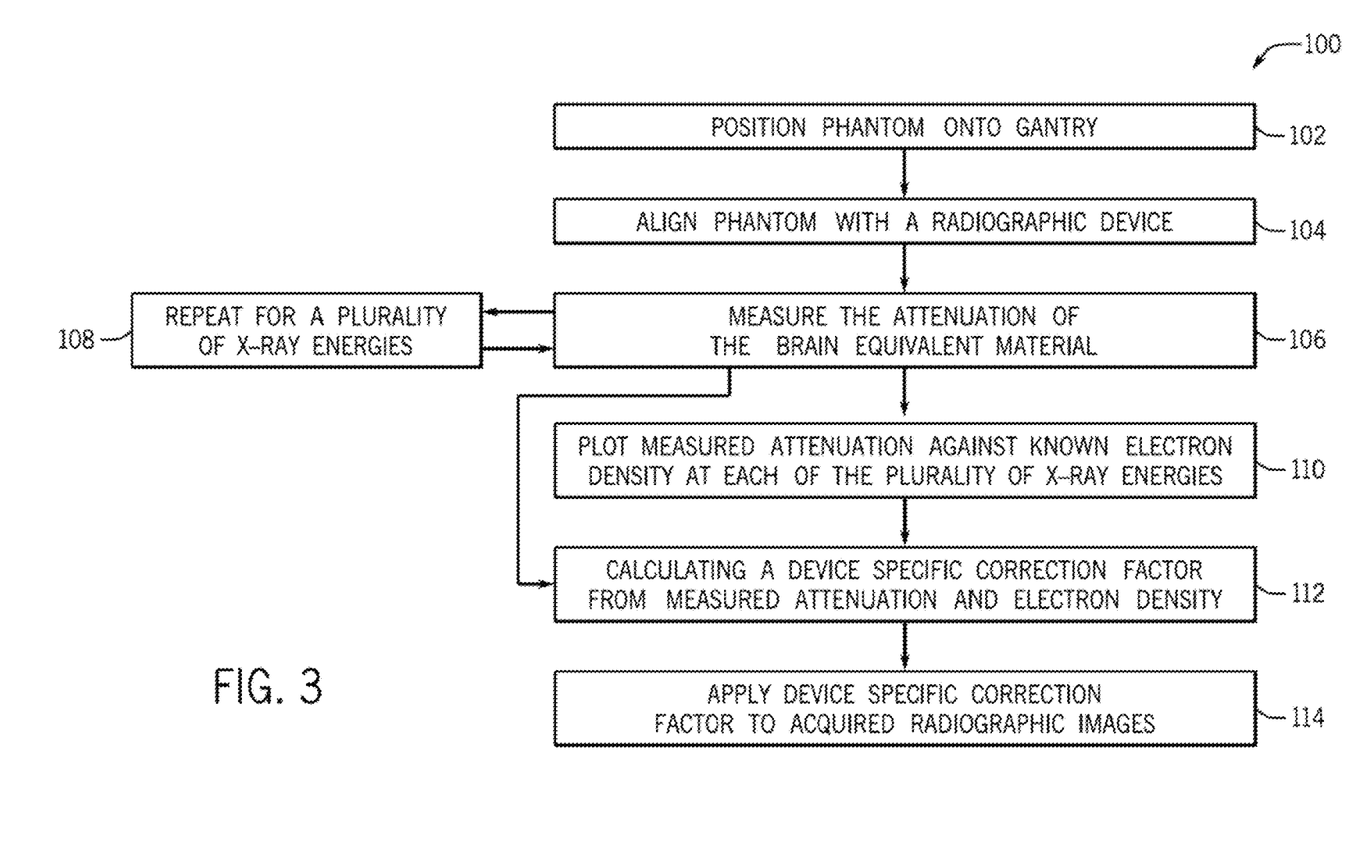
FIG. 3 is a flowchart that depicts an exemplary embodiment of a method of calibrating a radiographic device.

FIG. 3 is a flow chart that depicts an exemplary embodiment of a method 100 of calibrating a radiographic device for imaging brain tissue. In the calibration of method 100, a device specific correction factor is calculated in order to establish a relationship for a specific radiographic device between electron density ($\rho_3$) of various tissue and the corresponding CT number in Hounsfield units (HU). At 102, the phantom is positioned onto a gantry of a radiographic device. The phantom may include a plurality of tissue equivalent materials or inserts. In an embodiment, the phantom includes at least one brain equivalent material constructed in the compositions and/or manner as disclosed herein, although it will be recognized that in alternative embodiments, the phantom may comprise a plurality of a variety of tissue materials or inserts.

At 104 the phantom is aligned with the radiographic device for radiographic imaging, exemplarily CT imaging. In embodiments, the phantom may include visible or radiographically visible aligned markers to facilitate the alignment of the phantom with the radiographic device at 104. At 106 the attenuation of the brain equivalent material is measured with the radiographic device. In an exemplary embodiment, this measurement of the attenuation is represented in Hounsfield units in an exemplary embodiment, the attenuations are measured at 106 for each of the tissue equivalent materials in the phantom.

Optionally, at 108, the measurements are repeated for a plurality of X-ray energies. In an exemplary embodiment, the plurality of X-ray energies may include 40 keV-140 keV, while other ranges, including but not limited to, 10 keV-150 keV may also be used, while narrower ranges or measurement at 1, 2, or another predetermined number of specific X-ray energies are made. From these measurements at 106, a device specific correction factor may be calculated from the measured attenuation and the electron density. In an exemplary embodiment, the correction factor may be calculated. In an exemplary embodiment, the batho formula may exemplarily be used; correction factors equal TAR $\{TAR(d_2,A)/TAR(d_1,A)\}(\rho_e)^{-1}$ where a is the field area and $d_1$ and $d_2$ are the distances of the point of interest to the top and bottom of the heterogeneity. In embodiments, the correction factor may be calculated specifically for the device for correction of brain tissue, while in alternative embodiments, correction factors may be calculated for each of a plurality of different imaged tissues. In a still further embodiment, a generalized correction factor may be calculated for imaging of all tissue by the specific device.

Optionally, at 110 the measured attenuations maybe plotted against the known electron densities for each of the tissue equivalent materials. These plots may further be constructed at each of the plurality of X-ray energies at which the attenuation measurements are obtained. The plotting of the measured attenuation against normal electron densities at 110 may facilitate the calibration of the device specific correction factor at 112.

Finally, at 114 the device specific correction factor is applied to acquire radiographic images by the radiographic device to properly calibrate the CT number to the image tissues for that radiographic device.

FIGS. 4A-4D depict exemplary embodiments of auxiliary phantoms. The auxiliary phantoms as disclosed herein mimic an auxiliary tissue (e.g. a vessel, aneurysm, hematoma, or tumor) and in use may be embedded in an insert (e.g. 16, FIG. 1) of another tissue mimicking material which may surround the auxiliary tissue. In one example, the auxiliary phantom represents an aneurysm and is constructed of a blood-equivalent material and embedded in an insert of the newly disclosed brain equivalent material.

Figure 4A:
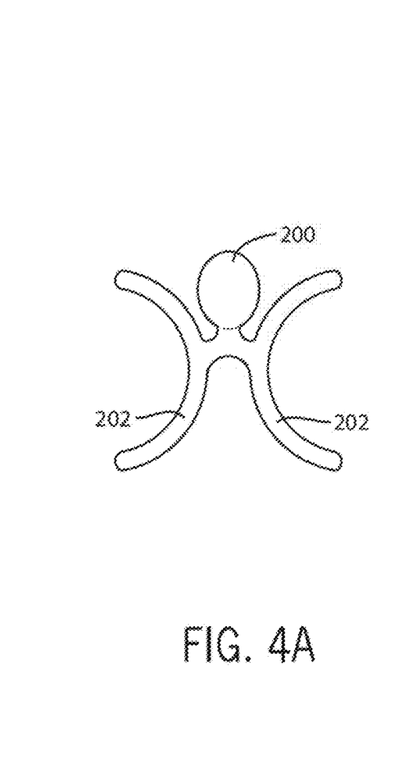
FIGS. 4A-D depict images of exemplary embodiments of auxiliary phantoms.
Figure 4B:
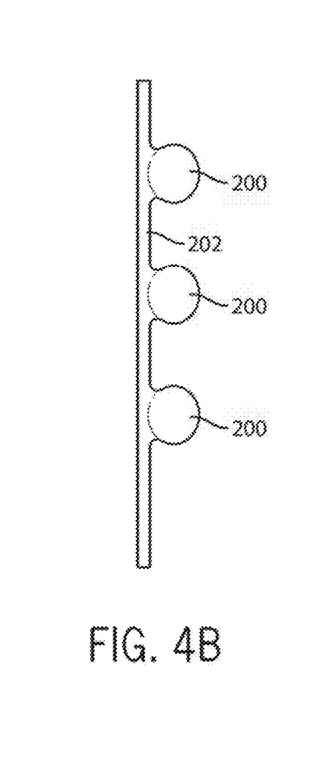
Figure 4C:
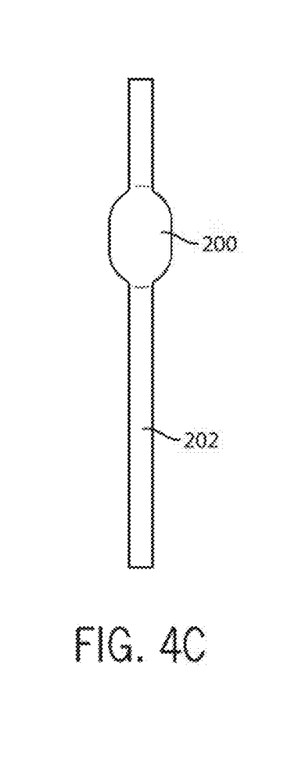
Figure 4D:
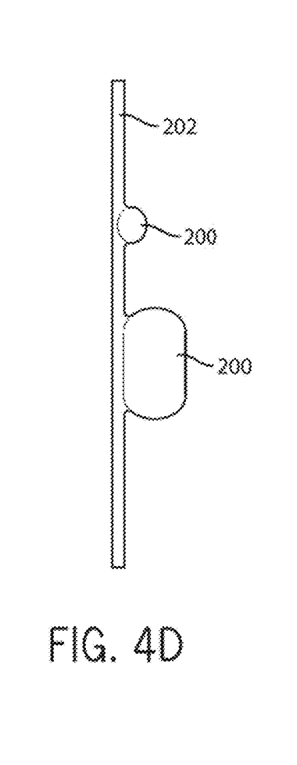

A brain aneurysm is a weak or thin spot on a blood vessel in the brain that balloons out and fills with blood. While aneurysms can occur anywhere in the brain, they most likely occur along a loop of arteries that run between the underside of the brain and the base of the skull. FIGS. 4A, 4B, and 4D depict exemplary embodiments of saccular aneurysms which include at least one aneurysm 200 and at least one vessel 202. FIG. 4A depicts an exemplary embodiment of an auxiliary phantom of a saccular aneurysm at a branching of vessels. FIG. 4B depicts an auxiliary of phantom of a vessel 202 with a series of aneurysms 200. FIG. 4D depicts an auxiliary phantom with a vessel having two aneurysms 200 of varying size. FIG. 4C depicts an auxiliary aneurysm of a vessel 202 with a fusiform aneurysm. Each of these auxiliary phantoms may be used for calibration of quality assurance purposes regarding relationships or quantification relative to vessels or other aneurysms, aneurysm position, or aneurysm size.

In an exemplary embodiment, one or more auxiliary phantoms may be used in connection with the new brain tissue material as described herein to improve CT capabilities and quality assurance for aneurysm detection and/or quantification. Aneurism shape and size are important to be known to predict evolution or confirm effectiveness of treatment. Use of an auxiliary phantom as disclosed herein can be to determine scanner presents to obtain an optimal image. A variety of size, shape, and morphological examples in auxiliary phantoms can further assist in technician training, machine set up and scanner validation. When measuring a volume of an auxiliary phantom (e.g. representative of a vessel, aneurysm, hematoma, or tumor) it is important to know the exact shape and dimensions of the auxiliary phantom, but also important to produce contrasts that match those of the real tissues. In these regards, a CT system can detect the boundaries and/or contours of the auxiliary phantom and a volume calculated from the detected contours. Thus, without an accurate representation of brain tissue and the auxiliary tissue (e.g. vessel, aneurysm, hematoma, or tumor) the CT systems, boundaries, and/or contour detection and volume determination cannot be calibrated or verified.

As noted above, brain aneurysms are commonly found on vessels between the brain and the base of the skull. While CT quality and techniques are available to commonly provide a rough assessment for aneurysms, most patients must still undergo a traditional cerebral angiogram for definitive diagnosis and to determine treatment. However, exemplarily with embodiments of the brain material and phantom as disclosed herein, an insert constructed of the disclosed new brain material and containing an auxiliary phantom approximating the identified aneurysm may be positioned relative to the skill-mimicking material of the first portion of the insert to approximate the condition of the aneurysm. After calibration and/or quality assurance of the CT system with respect to this phantom arrangement, Computed Tomography Angiography (CTA) may be performed to evaluate the aneurysm in the patient.

Figure 5:
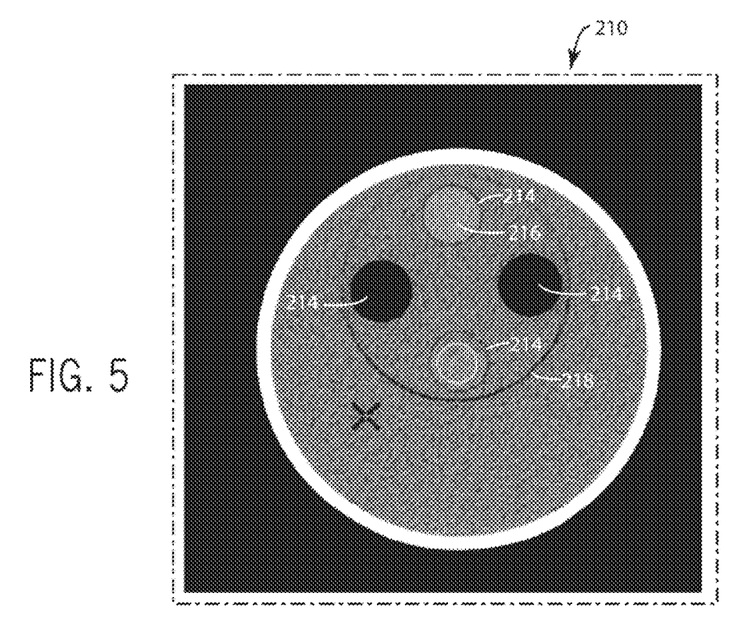
FIG. 5 depicts a CT image of an exemplary embodiment of a calibration device.
Figure 6:
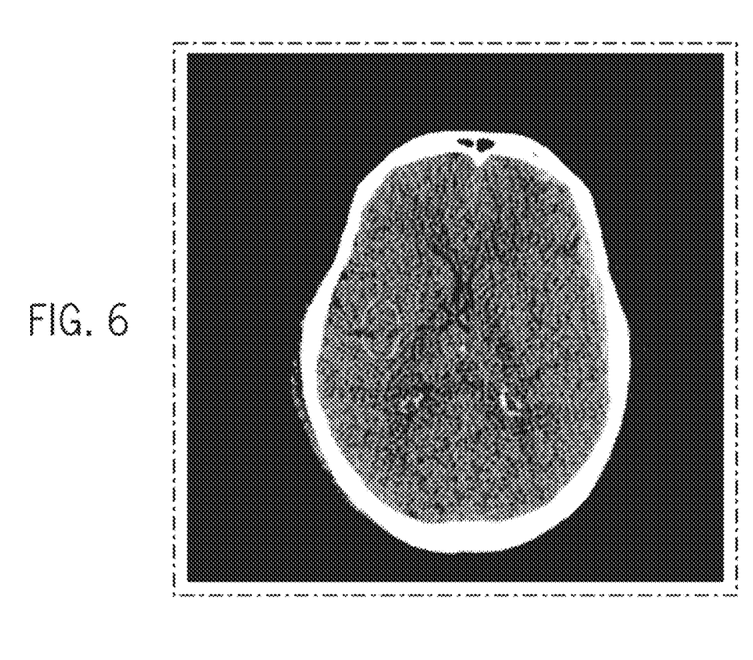
FIG. 6 depicts an exemplary CT image of a human brain.

FIG. 5 depicts a CT image of an exemplary embodiment of a calibration device 210. FIG. 6 depicts a CT image of a similar scan of a real human brain. The dial 218 can be seen as a discontinuity in the brain tissue equivalent material of the calibration device 210. The skull equivalent material is clearly seen on the exterior of the calibration device 210 as the first portion 220 as well as the relative positions of the inserts 216 within the dial 218 to the first portion 220. Slots 214 without inserts 216 appear black in the CT image due to the transmissivity of air.

As can be seen in FIG. 5 exemplary embodiments of the brain tissue equivalent material exhibit a natural inhomogeneity in CT number due to the composition of the material, including the acrylic micro spheres and glass micro bubbles. This can be seen by a comparison between the CT images of FIGS. 5 and 6. The inventors have found that in macro simulative imaging for calibration and quality assurance purposes, this inhomogeneity better mimics the natural inhomogeneity of real brain tissue, caused in part by the reticuli of the brain tissue.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A composition comprising:
1-4% glass micro bubbles (w/w);
60-80% (w/w) epoxy wherein the epoxy components are present in a 10:4 to 1:1 ratio of resin to polyamine or anhydride;
3-5% $CaCO_3$ (w/w);
1-3% MgO(w/w);
9-13% Polyethylene (w/w)
3-7% Acrylic Micro Spheres (w/w); and
0-1% Pigment.

2. The composition of claim 1, for use in radiographic calibration and quality assurance, wherein the concentration of glass micro bubbles is 1.6-3.6% (w/w) and the 60-80% (w/w) epoxy consists of:
50-63% Araldite (w/w); and
18-24% Jeffamine (w/w).

3. The composition of claim 1, wherein the elemental composition comprises:
Hydrogen at a concentration of 8-9% (w/w);
Carbon at a concentration of 67-68% (w/w);
Nitrogen at a concentration of 1-2% (w/w);
Oxygen at a concentration of 20-21% (w/w);
Chlorine at a concentration of less than 1% (w/w);
Calcium at a concentration of less than 1% (w/w); and
Silicon at a concentration of less than 1% (w/w).

4. The composition of claim 1, wherein the composition comprises at least one of boron, sodium or a combination thereof.

5. The composition of claim 4, wherein the boron is at a concentration of less than 1% (w/w) and the sodium is at a concentration of less than 1% (w/w).

6. The composition of claim 1, wherein the composition consists of:
8.56% Hydrogen;
67.46% Carbon;
1.85% Nitrogen;
20.52% Oxygen;
0.11% Chlorine;
0.75% Calcium;
0.64% Silicon;
0.02% Boron; and
0.1% Sodium.

7. The composition of claim 1, wherein the composition has a physical density of between 1.045 $g/cm^3$ and 1.055 $g/cm^3$.

8. The composition of claim 1, wherein the composition is a brain tissue phantom.

9. The composition of claim 1, wherein the composition mimics radiographic attenuation of brain tissue within ±5 HU for X-ray energies between 40 keV and 140 keV.

10. The composition of claim 9, wherein the composition mimics radiographic attenuation of brain tissue with ±1 HU for X-ray energies between 40 keV and 140 keV.

11. The composition of claim 1, wherein the epoxy resin is selected from Araldite, trimethylhexamethylenediamine, Epoxide No. 7, Epikote and combinations thereof and the hardener is selected from Jeffamine, Synolide, aminohexanes, polyoxypropylenetriamines or combinations thereof.

12. A method of calibrating a radiographic device for imaging of brain tissue, the method comprising:
   providing a phantom with a brain equivalent material comprising the composition of claim 1;
   aligning the phantom with the radiographic device;
   measuring an attenuation of X-rays by the brain equivalent material; and
   calculating a device specific correction factor for the radiographic device from the measured attenuation of the X-rays and a known electron density for the brain equivalent material.

13. The method of claim 12, further comprising repeating the measurement of the attenuation of the X-rays at a plurality of X-ray energies.

14. The method of claim 12, wherein the plurality of X-ray energies are between 40 keV and 140 keV.

15. The method of claim 13, wherein the phantom comprises a plurality of tissue equivalent materials, and further comprising:
   measuring an attenuation of the X-rays by each of the plurality of tissue equivalent materials;
   plotting the measured attenuations of the X-rays by the tissue equivalent materials and the brain equivalent material against known electron densities for the plurality of tissue equivalent materials and the brain equivalent material; and
   wherein the device specific correction factor is calculated from the measured attenuations and the known electron densities.

16. The method of claim 12, wherein the brain equivalent material is the composition of claim 6.

17. The method of any one of claims 12, further comprising applying the device specific correction factor to radiographic images acquired by the radiographic device.

18. A composition comprising:
   1-4% glass micro bubbles (w/w);
   60-80% (w/w) epoxy wherein the epoxy components are present in a 10:4 to 1:1 ratio of resin to polyamine or anhydride;
   3-5% $CaCO_3$ (w/w);
   1-3% MgO(w/w); and
   9-13% Polyethylene (w/w)
   wherein the composition consists of:
      8. 56% Hydrogen;
      67. 46% Carbon;
      1. 85% Nitrogen;
      20. 52% Oxygen;
      0.11% Chlorine;
      0.75% Calcium;
      0.64% Silicon;
      0.02% Boron; and
      0.1% Sodium.

* * * * *